US012303397B2

(12) United States Patent
Wolfe et al.

(10) Patent No.: US 12,303,397 B2
(45) Date of Patent: *May 20, 2025

(54) MESH SPACER HYBRID

(71) Applicant: Spineology Inc., St. Paul, MN (US)

(72) Inventors: Steve Wolfe, Woodbury, MN (US);
Bryan Becker, Richfield, MN (US);
Tim Walnofer, Stillwater, MN (US);
Clint Boylan, Minneapolis, MN (US);
Dan McPhillips, Andover, MN (US);
Michael Wang, Miami, FL (US); Craig Kuhns, Columbia, MO (US); Garrett Ganske, Lino Lakes, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,766

(22) Filed: Dec. 4, 2023

(65) Prior Publication Data
US 2024/0173144 A1  May 30, 2024

Related U.S. Application Data

(63) Continuation of application No. 17/577,242, filed on Jan. 17, 2022, now Pat. No. 11,833,058, which is a (Continued)

(51) Int. Cl.
*A61F 2/44* (2006.01)
*A61F 2/28* (2006.01)
(Continued)

(52) U.S. Cl.
CPC ............ *A61F 2/441* (2013.01); *A61F 2/2846* (2013.01); *A61F 2/442* (2013.01); *A61F 2/4425* (2013.01); *A61F 2/4455* (2013.01); *A61F 2/446* (2013.01); *A61F 2002/2835* (2013.01); *A61F 2002/30004* (2013.01); *A61F 2002/30011* (2013.01); *A61F 2002/30014* (2013.01); *A61F 2002/30019* (2013.01); *A61F 2002/30329* (2013.01);
(Continued)

(58) Field of Classification Search
CPC ................ A61F 2/441; A61F 2002/448; A61F 2002/4485; A61F 2002/4495
See application file for complete search history.

(56) References Cited

U.S. PATENT DOCUMENTS 7,534,268 B2 * 5/2009 Hudgins ................. A61F 2/441
606/279
9,687,356 B1 * 6/2017 Spangler ............... A61F 2/4611
(Continued)

*Primary Examiner* — Nicholas W Woodall
(74) *Attorney, Agent, or Firm* — Getz Balich LLC

(57) ABSTRACT

A method of placing an implant for intervertebral fusion between adjacent vertebral bodies in a patient includes inserting the implant in a space between the adjacent vertebral bodies such that both a first intervertebral spacer body and a second intervertebral spacer body contact each of the adjacent vertebral bodies. The first intervertebral spacer body is spaced apart from the second intervertebral spacer body. An expandable container portion of the implant disposed between the first intervertebral spacer body and the second intervertebral spacer body is filled with fill material such that the expandable container expands to contact each of the adjacent vertebral bodies.

20 Claims, 10 Drawing Sheets

Related U.S. Application Data continuation of application No. 16/173,727, filed on Oct. 29, 2018, now Pat. No. 11,224,520, which is a continuation of application No. 15/078,959, filed on Mar. 23, 2016, now Pat. No. 10,111,756, which is a continuation of application No. 13/951,162, filed on Jul. 25, 2013, now abandoned.

(60) Provisional application No. 61/675,668, filed on Jul. 25, 2012, provisional application No. 61/793,923, filed on Mar. 15, 2013.

(51) Int. Cl.
 *A61F 2/30* (2006.01)
 *A61F 2/46* (2006.01)

(52) U.S. Cl.
 CPC ........ *A61F 2002/30484* (2013.01); *A61F 2002/30485* (2013.01); *A61F 2002/30581* (2013.01); *A61F 2002/30588* (2013.01); *A61F 2002/30593* (2013.01); *A61F 2002/30604* (2013.01); *A61F 2002/30607* (2013.01); *A61F 2002/30616* (2013.01); *A61F 2002/30624* (2013.01); *A61F 2002/443* (2013.01); *A61F 2/447* (2013.01); *A61F 2002/448* (2013.01); *A61F 2002/4485* (2013.01); *A61F 2002/4495* (2013.01); *A61F 2/4603* (2013.01); *A61F 2002/4692* (2013.01); *A61F 2210/0061* (2013.01); *A61F 2250/0003* (2013.01)

(56) References Cited

U.S. PATENT DOCUMENTS

| | | | |
|---|---|---|---|
| 9,730,803 B2* | 8/2017 | DiMauro | A61L 27/12 |
| 2005/0113919 A1* | 5/2005 | Cragg | A61F 2/442 |
| | | | 623/17.11 |
| 2008/0154305 A1* | 6/2008 | Foley | A61B 17/7065 |
| | | | 606/279 |

* cited by examiner

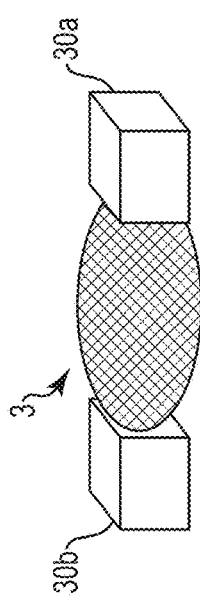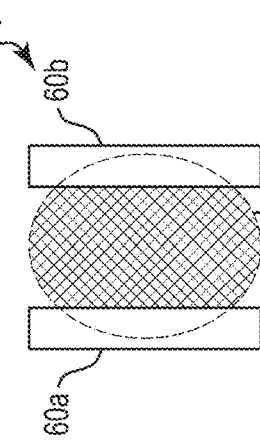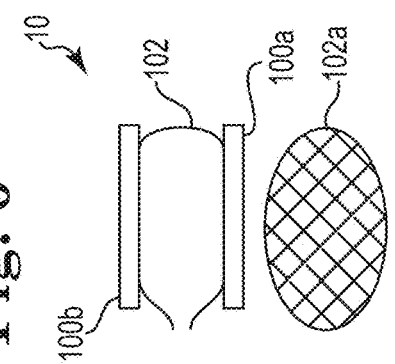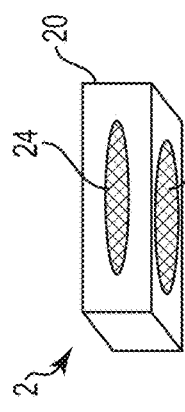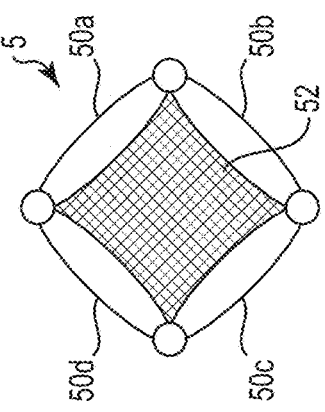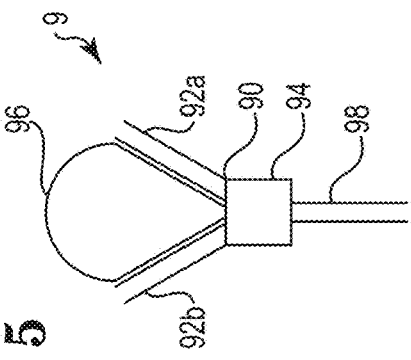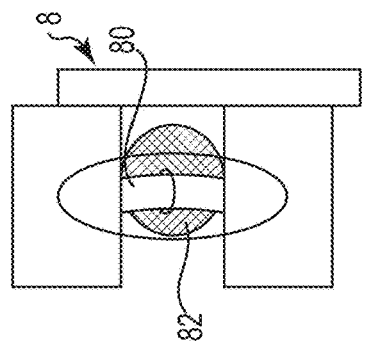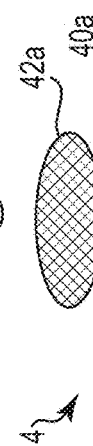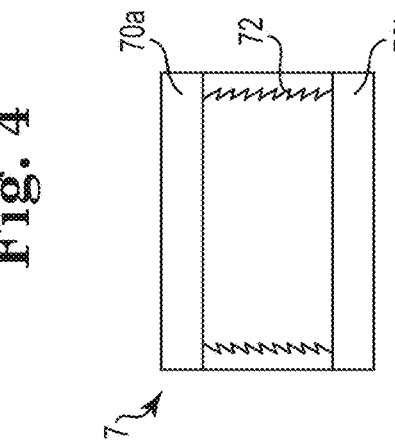

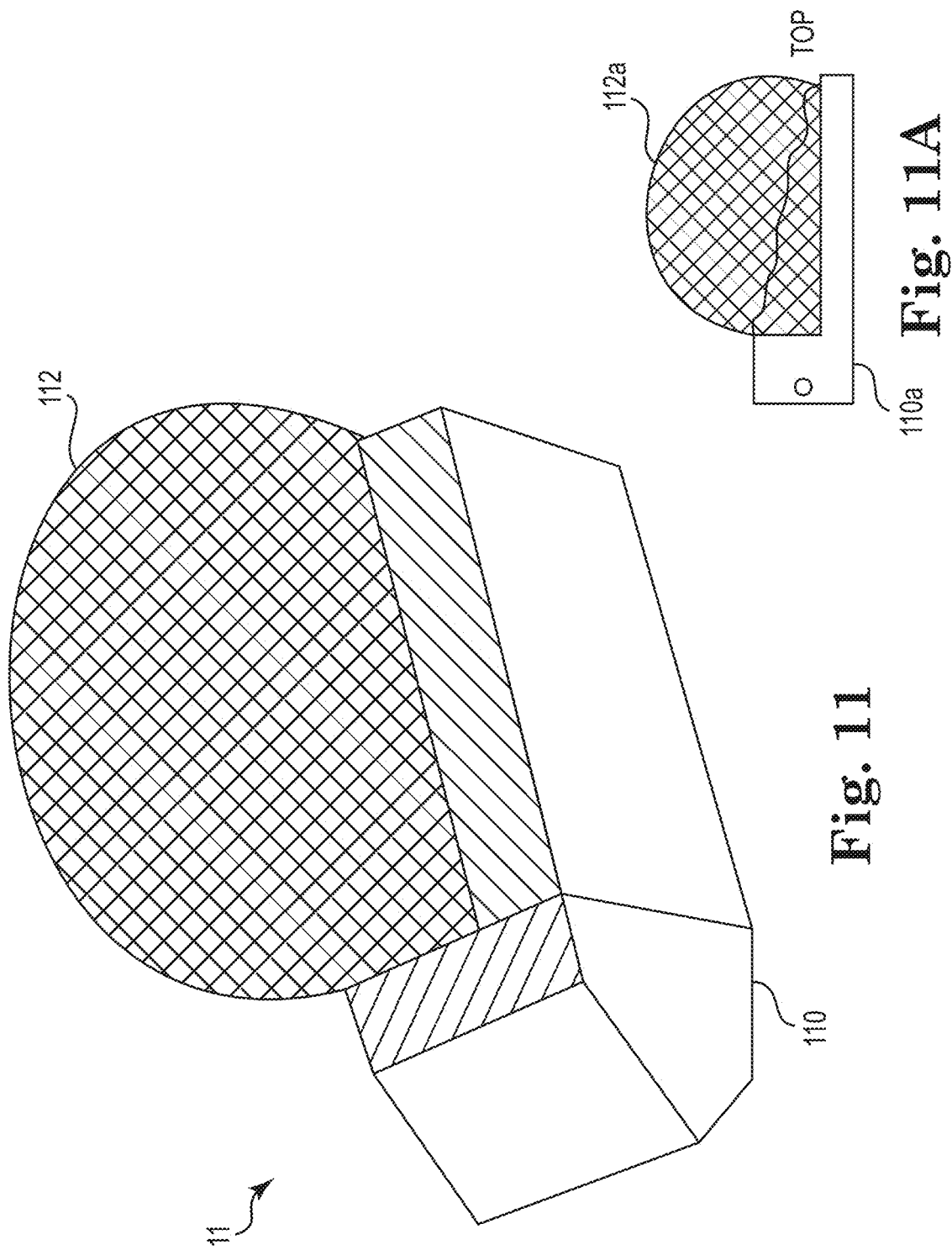

MESH SPACER HYBRID

PRIORITY

This application is a continuation of U.S. patent application Ser. No. 17/577,242, filed Jan. 17, 2022, which is a continuation of U.S. patent application Ser. No. 16/173,727, filed Oct. 29, 2018, which is a continuation of U.S. patent application Ser. No. 15/078,959, filed Mar. 23, 2016, which is a continuation of U.S. patent application Ser. No. 13/951,162, filed Jul. 25, 2013, which claims the priority benefit of U.S. Provisional Application Ser. No. 61/675,668, filed on Jul. 25, 2012 and the priority benefit of U.S. Provisional Application Ser. No. 61/793,923, filed on Mar. 15, 2013, and all of foregoing are hereby incorporated herein by reference in their entirety.

FIELD

The present invention generally relates to a PEEK spacer/Mesh container hybrid for use in the spine. More particularly, the present invention relates to a PEEK spacer/Mesh container hybrid configured to be placed in the spine via a percutaneous or minimally invasive access opening.

BACKGROUND

PEEK spacers are commonly used in spine surgery, particularly fusion surgery. Often bone graft or other fill material is used with a spacer to help promote bony fusion. It is desirable that the fill material contacts the vertebral endplates while the spacer provides structural support. In an attempt to minimize the size of spacers, traditional PEEK spacers lack adequate cavities for fill material insertion. As such, fill material is often packed around the spacer, rather than in the spacer. Uncontained fill material does pose a risk of migrating to surrounding anatomy which can lead to patient injury.

It is desirable to have a spacer small enough to be inserted via a minimally invasive or even percutaneous approach, while allowing for greater fill material containment and fill material contact with the vertebral endplates. There is a need for a PEEK spacer that is small enough to fit through an MIS or percutaneous approach, yet able to expand upon insertion to fully support and/or stabilize the intervertebral space while containing fill material therewithin.

SUMMARY

The present invention, according to certain embodiments, comprises a modular implant for performing an intervertebral fusion on adjacent vertebral bodies in a patient. The implant includes a first spacer portion, a second spacer and a container having a first end and a second end, the first end of the container constructed to operably engage a first spacer and the second end of the container constructed to operably engage the second spacer.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 1 depicts a perspective view of an embodiment of the present invention.

FIG. 2 depicts a perspective view of an embodiment of the present invention.

FIG. 3 depicts a perspective view of an embodiment of the present invention

FIG. 4 depicts a perspective view of an embodiment of the present invention

FIG. 5 depicts a perspective view of an embodiment of the present invention.

FIG. 6 depicts a perspective view of an embodiment of the present invention.

FIG. 7 depicts a perspective view of an embodiment of the present invention.

FIG. 8 depicts a perspective view of an embodiment of the present invention.

FIG. 9 depicts a perspective view of an embodiment of the present invention.

FIG. 10 depicts a perspective view of an embodiment of the present invention.

FIG. 11 depicts a perspective view of an embodiment of the present invention.

FIG. 11a depicts a top perspective view of the embodiment of the present invention depicted in FIG. 11.

Figure 12:
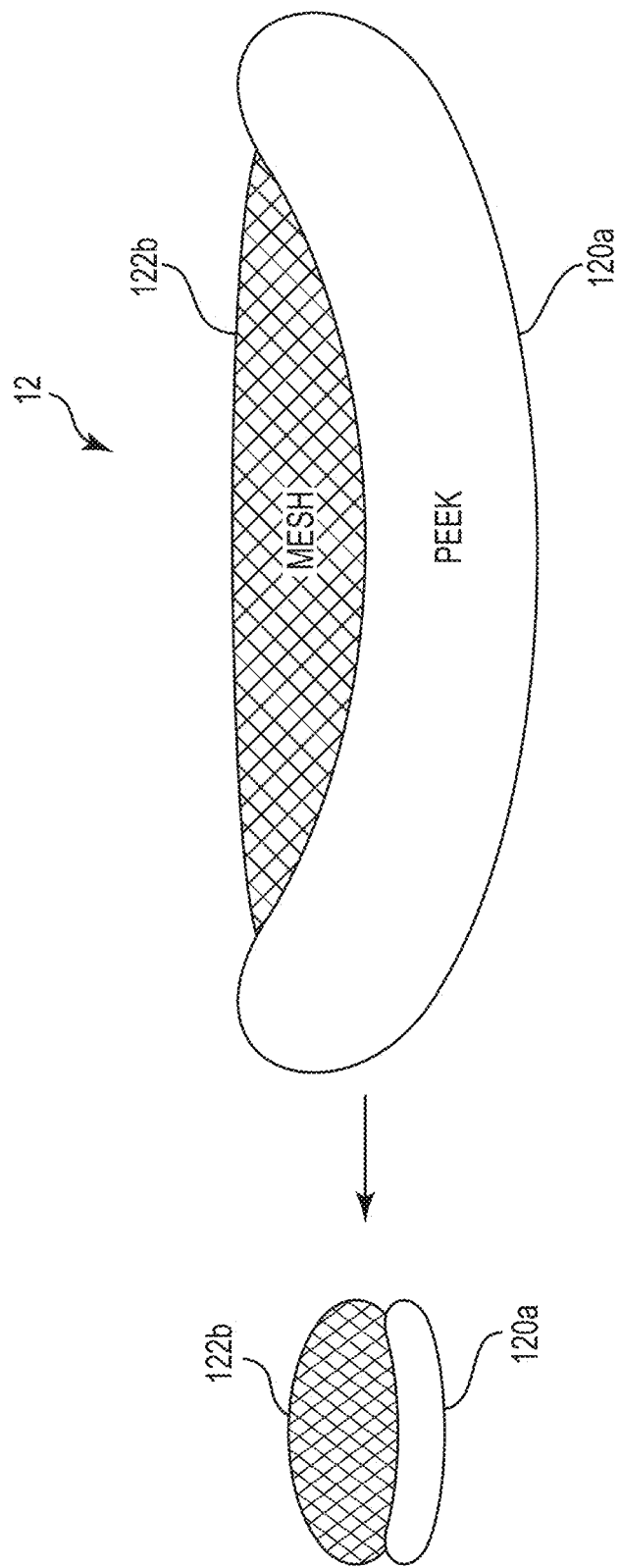
FIG. 12 depicts a perspective view of an embodiment of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

As shown in FIGS. 1-17, an embodiment of the present invention may include a spacer body and a container attached or otherwise operably connected to the spacer body. The spacer may be comprised of PEEK or any other biocompatible material or combination thereof. Spacer body may provide structural support between the adjacent vertebrae. The container may be comprised of PET or any other biocompatible material or combination thereof. The container may be comprised of material such that the container is flexible and/or conformable to the patient's anatomy.

The container may contain bone graft, bone substitute or any other biocompatible fill material. Such fill material may promote bony fusion. The container may be porous to allow the fill material to contact the vertebral endplates, promoting bony fusion. According to an embodiment of the present invention, the spacer hybrid of the present invention may be inserted into an intervertebral disc space in a first unexpanded configuration and then the container portion of the device may be filled with fill material expanding the device to a second expanded configuration. According to another embodiment, mechanical tools may be used to open the device of the present invention from a first unexpanded configuration to a second expanded configuration. Expansion of the hybrid device may distract the adjacent vertebrae.

FIG. 1 depicts an embodiment of the hybrid device 1 of the present invention which may include a PEEK spacer portion 10 and a container portion 16. PEEK portion 10 may include a body 14 and arms 12a and 12b movably connected to body 14. Container 16 may be configured to receive and contain biocompatible fill material. Hybrid device 1 of this embodiment may be inserted between two vertebrae in a collapsed state and expanded upon the introduction of fill material into container 16 and/or by mechanical tools.

FIG. 2 depicts another embodiment of a hybrid fusion device 2 according to the present invention. The embodiment depicted in FIG. 2 may include a spacer portion 20 comprised of PEEK or other biocompatible material. Spacer portion 20 may include at least one opening 24. Hybrid device 2 may also include a container 22 disposed therewithin. Container 22 may be configured to receive and contain biocompatible fill material.

FIG. 3 depicts yet another embodiment of the hybrid device 3 of the present invention. Hybrid device 3 may include spacer body portions 30a and 30b. According to this embodiment, container 32 may be disposed between spacer body portions 30a and 30b. At least one of spacer body portions 30a and 30b may include a fill opening or port to facilitate filling container 32 with fill material. Hybrid device 3 may be inserted into an intervertebral space in an unexpanded position and expanded in situ by the insertion of fill material into container 32 and/or by mechanical tools.

FIG. 4 depicts a hybrid device 4 according to the present invention. Hybrid device 4 may include a curved spacer body 40 configured to fit adjacent container 42 in an intervertebral space.

FIG. 5 depicts yet another hybrid device 5 according to the present invention. Hybrid device 5 includes spacer body portions 50a-d. Spacer body portions 50a-d may be movably connected to each other. Such movable connection may be a pivot or other desired connection. Hybrid device 5 may include any desired number of body portions as such, the four body portions depicted in FIG. 5 is merely illustrative. Container 52 may be disposed within spacer body portions such that container 52 may receive and contain fill material. Hybrid device 5 may be inserted into an intervertebral space in an unexpanded position and expanded in situ by the insertion of fill material into container 52 and/or by mechanical tools.

FIG. 6 depicts another embodiment of a hybrid device 6 of the present invention. Hybrid device 6 may include spacer portions 60a and 60b. Container 62 may be disposed between spacer portions 60a and 60b. Spacer portions 60a and 60b may be configured to contact adjacent vertebral endplates. Hybrid device 6 may be inserted into an intervertebral space in an unexpanded position and expanded in situ by the insertion of fill material into container 62 and/or by mechanical tools.

FIG. 7 depicts an alternate embodiment of hybrid device 7 according to the present invention. Hybrid device 7 may include spacer portions 70a and 70b and container portion 72. Once hybrid device 7 is placed in an intervertebral space, container portion 72 may be configured to facilitate the distraction of adjacent vertebrae. Container portion 72 may be filled with fill material in situ. Upon filling, container 72 may exert pressure on spacer portions 70a and 70b thereby distracting and/or moving adjacent vertebral endplates. Hybrid device 7 may be inserted into an intervertebral space in an unexpanded position and expanded in situ by the insertion of fill material into container 72 and/or by mechanical tools.

FIG. 8 depicts yet another hybrid device 8 according to the present invention. Device 8 may include spacer 80 and container portion 82. Container portion 82 may be connected to spacer portion 80 such that upon filling, container portion 82 expands outwardly from spacer portion 80. Hybrid device 8 may be inserted into an intervertebral space in an unexpanded position and expanded in situ by the insertion of fill material into container 82 and/or by mechanical tools.

FIG. 9 is another view of an embodiment of a hybrid device 9 according to the present invention. Device 9 includes a spacer portion 90 having movable arms 92a and 92b and body portion 94. Container 96 may be connected to spacer 90 such that container 96 may receive fill material upon insertion into the intervertebral space. Hybrid device 9 may be inserted into an intervertebral space in an unexpanded position and expanded in situ by the insertion of fill material into container 92 and/or by mechanical tools.

FIG. 10 depicts an alternate view of hybrid device 10 according to the present invention. Hybrid device 10 may include spacer portions 100a and 100b and container portion 102. Once hybrid device 10 is placed in an intervertebral space, container portion 102 may be configured to facilitate the distraction of adjacent vertebrae. Container portion 102 may be filled with fill material in situ. Upon filling, container 102 may exert pressure on spacer portions 100a and 100b thereby distracting and/or moving adjacent vertebral endplates. Hybrid device 10 may be inserted into an intervertebral space in an unexpanded position and expanded in situ by the insertion of fill material into container 102 and/or by mechanical tools.

FIG. 11 depicts yet another embodiment of the present invention. Device 11 may include spacer portion 110 and container portion 112. Hybrid device 11 may be inserted into an intervertebral space in an unexpanded position and expanded in situ by the insertion of fill material into container 112 and/or by mechanical tools.

FIG. 12 depicts a hybrid device 12 according to the present invention. Hybrid device 12 may include a curved spacer body 120 configured to fit adjacent container 122 in an intervertebral space. FIG. 12 depicts an unexpanded container 122 and an expanded container 122b. Hybrid device 12 may be inserted into an intervertebral space in an unexpanded position and expanded in situ by the insertion of fill material into container 122 and/or by mechanical tools.

Figure 13:
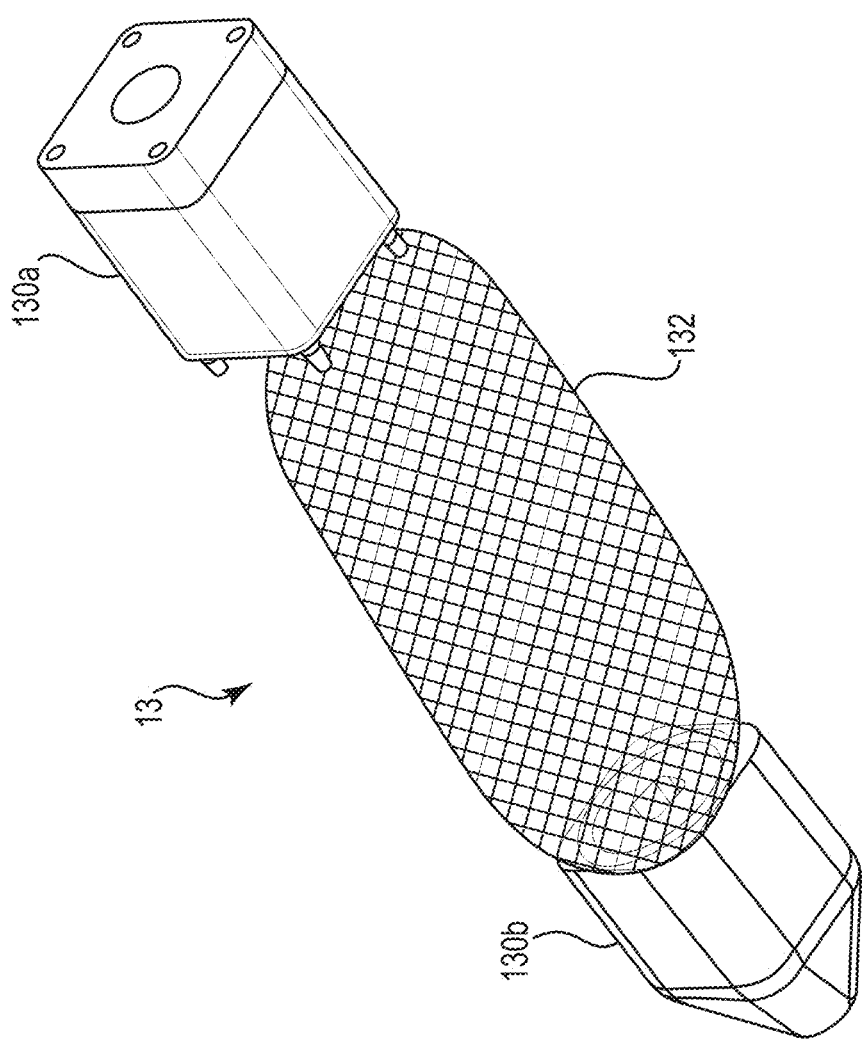
FIG. 13 depicts a perspective view of an embodiment of the present invention.

FIG. 13 depicts an expanded view of an embodiment of the present invention. Hybrid device 13 may include spacer portions 130a and 130b. According to this embodiment, container 132 may be disposed between spacer body portions 130a and 130b. At least one of spacer body portions 130a and 130b may include a fill opening or port to facilitate filling container 132 with fill material. Hybrid device 13 may be inserted into an intervertebral space in an unexpanded position and expanded in situ by the insertion of fill material into container 132 and/or by mechanical tools.

Figure 14:
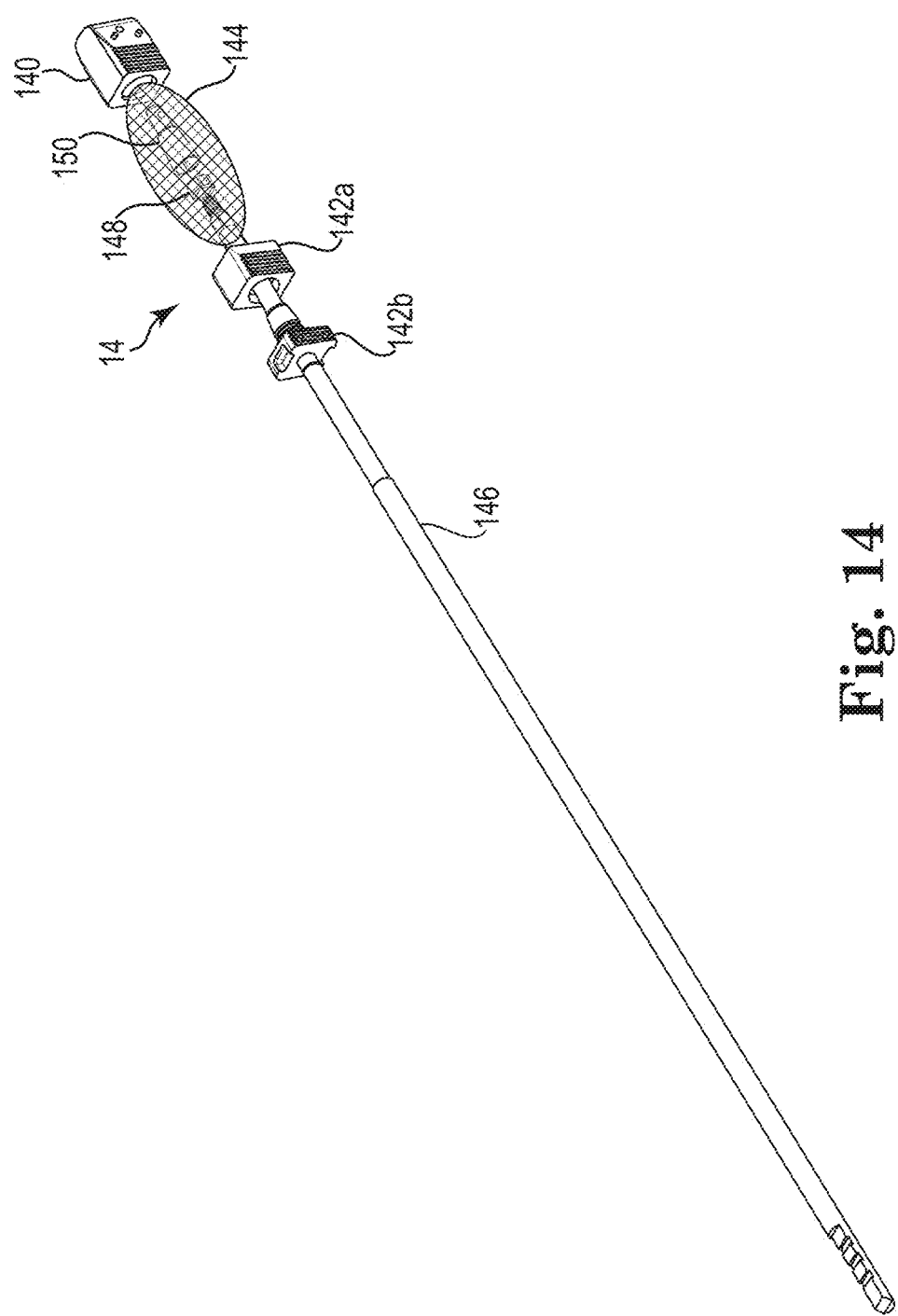
FIG. 14 depicts a perspective view of an embodiment of the present invention.
Figure 15:
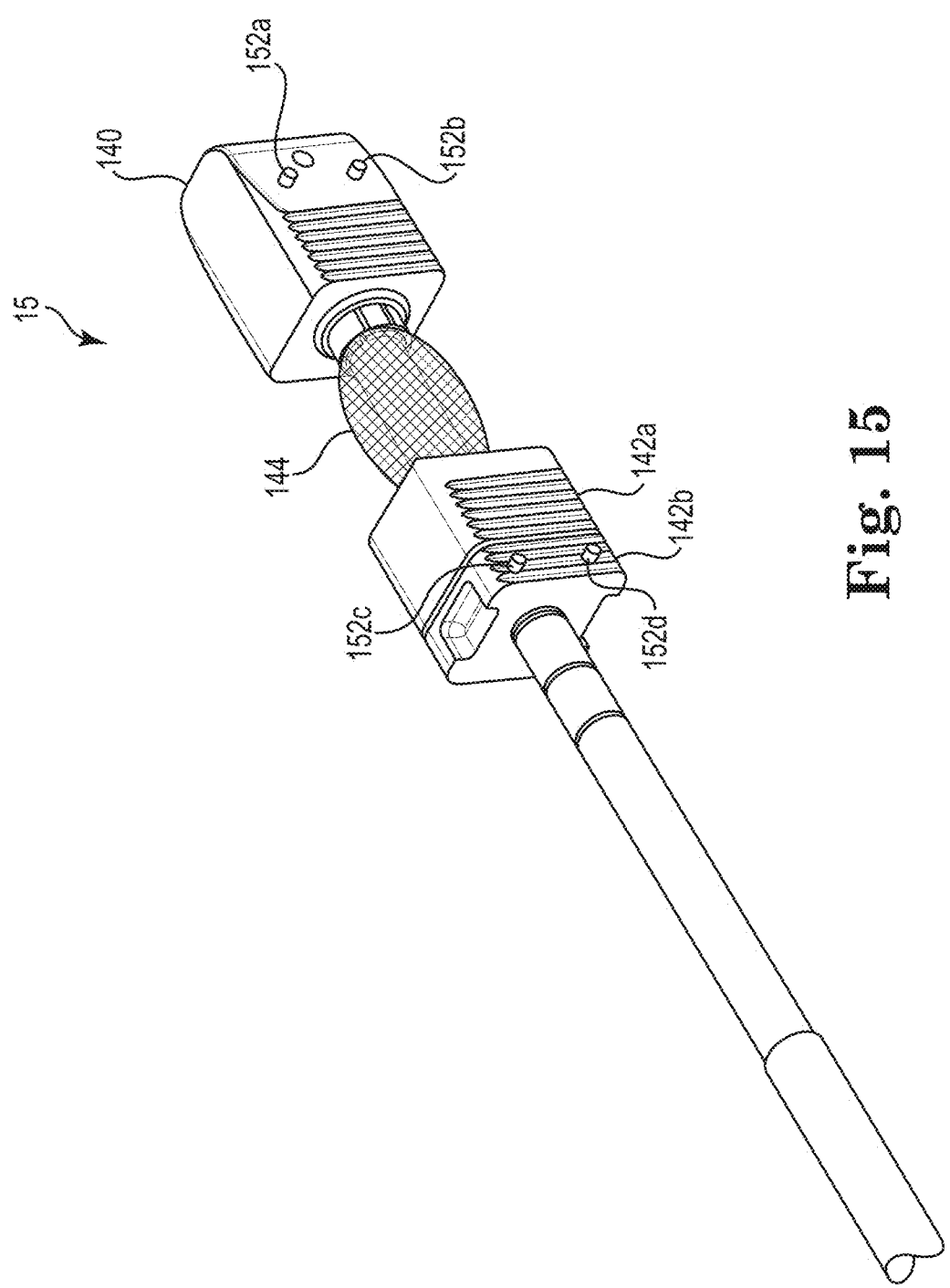
FIG. 15 depicts a perspective view of an embodiment of the present invention.
Figure 16:
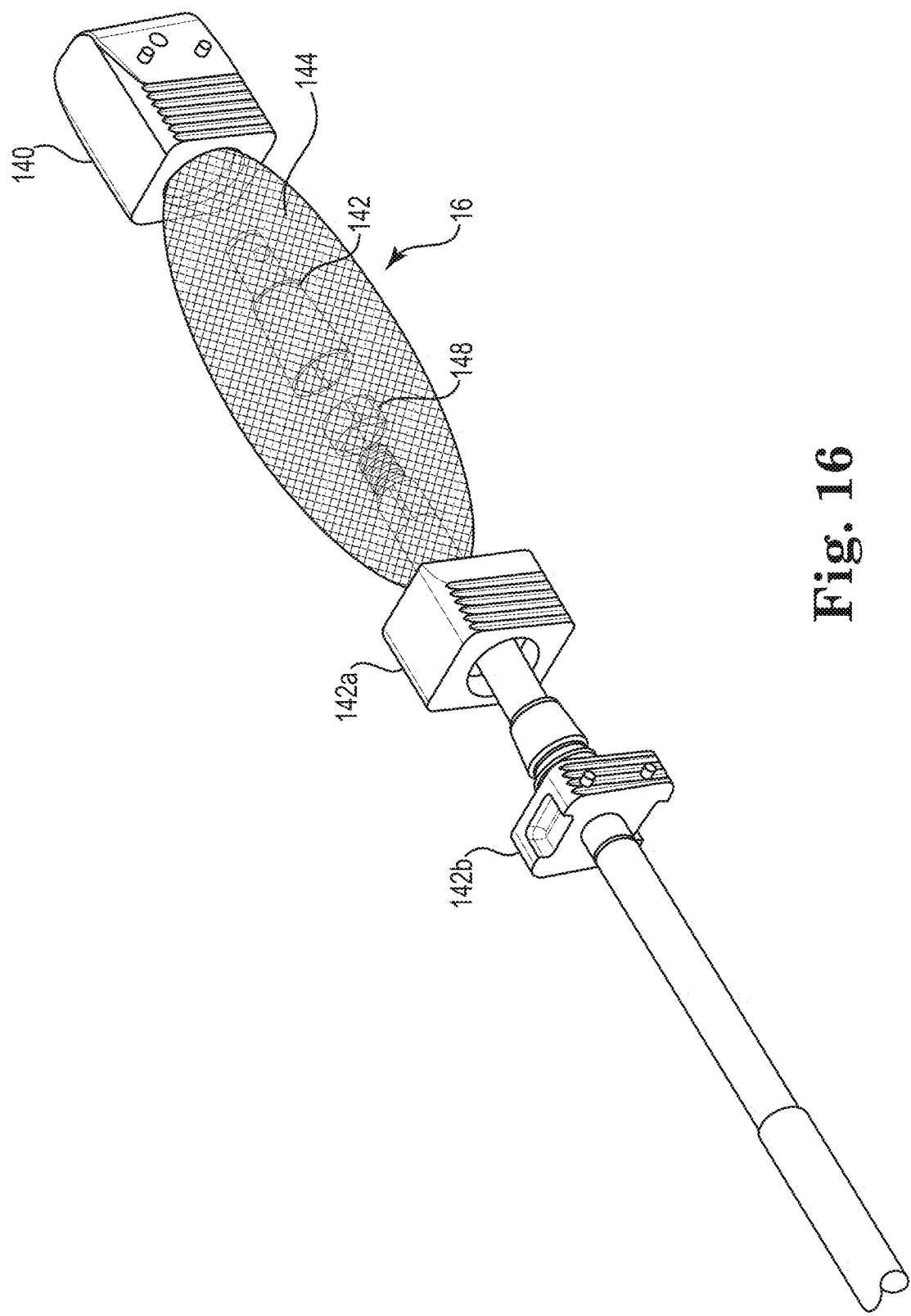
FIG. 16 depicts a perspective view of an embodiment of the present invention.

FIG. 14-16 depict an embodiment of the present invention, hybrid devices 14-16 respectively, wherein a first spacer body 140 is configured to receive a first end of container 144 and a second spacer body 142a and 142b is configured to receive a second end of container 144. The first and second spacer bodies may be comprised of one or more parts. An insertion rod 146 may insert the container into the first and second spacer bodies. Rod 146 may include an anti-rotation locking ring 148 that engages with the distal tip of inner 150. Once the locking ring 148 is engaged, the implant will not rotate. Ring 148 may be disengaged to allow implant rotation.

Spacer bodies 140 and 142 may include markings 152a-d which may allow visualization of the implant upon imaging. Markings 152a-d may project outward to engage the surrounding anatomy. Spacer bodies 140 and 142 may include other desired outward projections to engage the surrounding anatomy.

Spacer bodies 140 and 142 may include grooves on their inner diameters and utilize locking rings to receive and retain container 144. Other retention mechanisms may be used.

In use, the implant may be inserted into a prepared intervertebral cavity. The implant may be inserted with an empty container such that the implant may be placed through a MIS or percutaneous approach. Once placed, container 144 may be filled with bone graft or any combination of desired fill materials. In an embodiment, at least one of spacer bodies 140 and 142 may include a fill opening or a fill port, such that fill material may be placed into container 144. In another embodiment, fill material may be placed directly into container 144. As container 144 is filled, first spacer body 140 and second spacer body 142 may move apart creating an appropriate implant footprint for the particular patient's anatomy. First spacer body 140 and second spacer body 142 may provide structural support on the strongest part of the adjacent vertebrae. While container 144 may provide graft and fill material containment and further may provide a scaffold for bone growth and fusion because container 144 is placed in the most vascular part of the adjacent vertebra.

Hybrid devices 14-16 may be inserted into an intervertebral space in an unexpanded position and expanded in situ by the insertion of fill material into container 144 and/or by mechanical tools.

Figure 17:
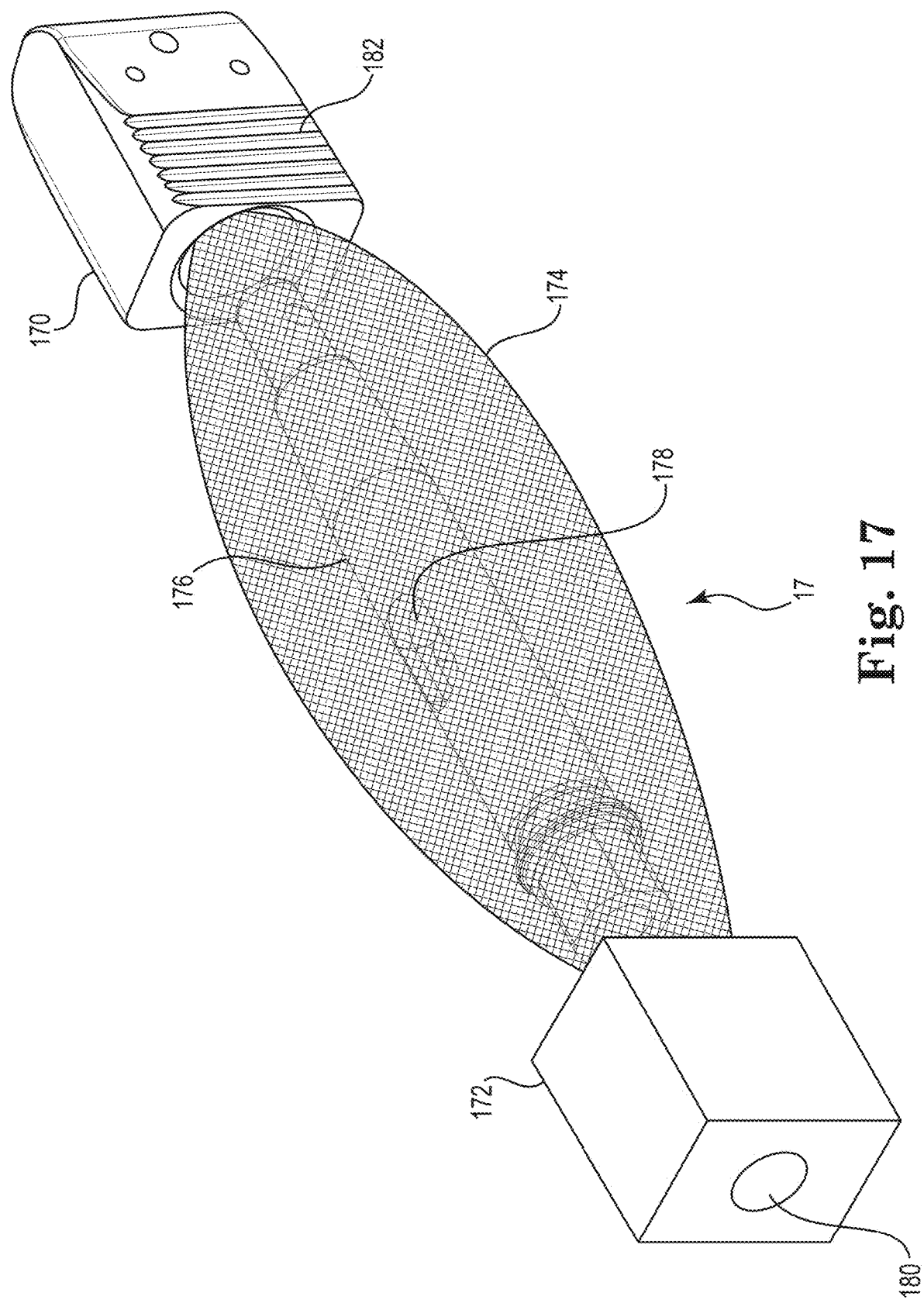
FIG. 17 depicts a perspective view of an embodiment of the present invention.

FIG. 17 depicts a hybrid device 17 according to another embodiment of the present invention. Hybrid device 17 may include spacer body portions 170 and 172. Container 174 may be disposed between spacer body portions 170 and 172. First spacer body 170 is configured to receive a first end of container 174 and a second spacer body 172 is configured to receive a second end of container 174. The first and second spacer bodies may be comprised of one or more parts. Hybrid device 17 may further include at least one connecting rod 176. Connecting rod 176 may connect spacer 170 to spacer 172. Connecting rod 176 may lock container 174 into position within spacer bodies 170 and 172. Connecting rod 176 may include a fill opening 178.

Spacer bodies 170 and 172 may include markings which may allow visualization of the implant upon imaging. Markings may project outward to engage the surrounding anatomy. Spacer bodies 170 and 172 may include other desired outward projections 182 to engage the surrounding anatomy.

Spacer bodies 170 and 172 may include grooves on their inner diameters and utilize locking rings to receive and retain container 174. Other retention mechanisms may be used.

In use, the implant may be inserted into a prepared intervertebral cavity. The implant may be inserted with an empty container such that the implant may be placed through a MIS or percutaneous approach. Once placed, container 174 may be filled with bone graft or any combination of desired fill materials. In an embodiment, at least one of spacer bodies 170 and 172 may include a fill opening or a fill port 180, such that fill material may be placed into container 174. In another embodiment, fill material may be placed directly into container 174. As container 174 is filled, first spacer body 170 and second spacer body 172 may move apart creating an appropriate implant footprint for the particular patient's anatomy. First spacer body 170 and second spacer body 172 may provide structural support on the strongest part of the adjacent vertebrae. While container 174 may provide graft and fill material containment and further may provide a scaffold for bone growth and fusion because container 174 is placed in the most vascular part of the adjacent vertebra.

Figure 18:
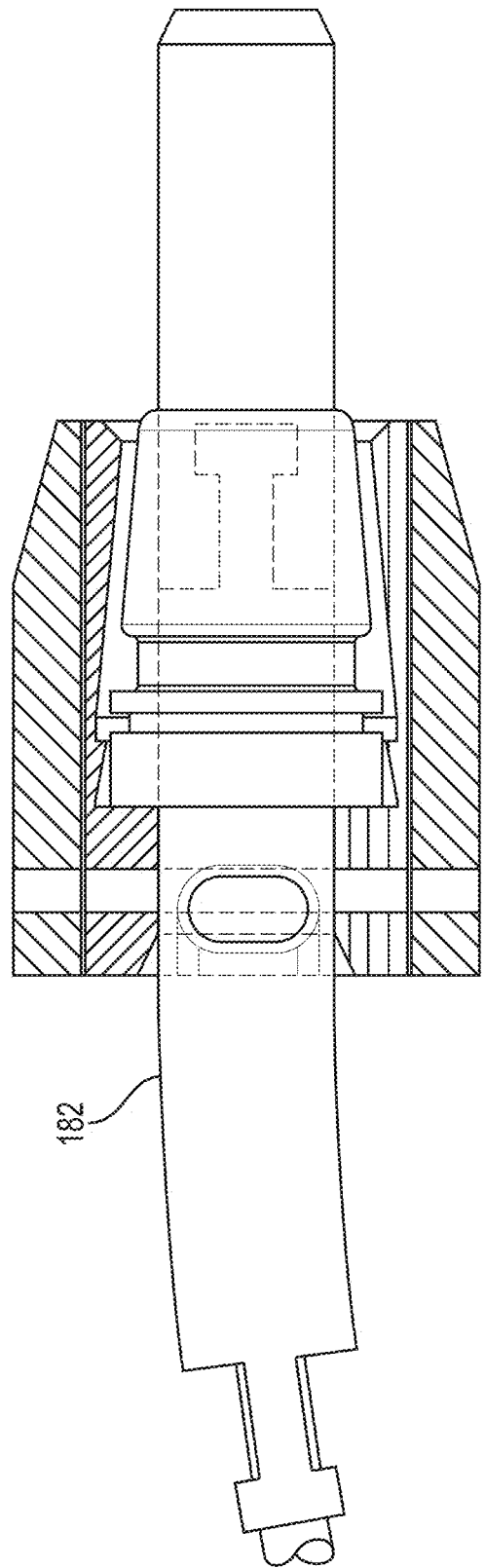
FIG. 18 depicts a perspective view of an embodiment of the present invention.
Figure 19:
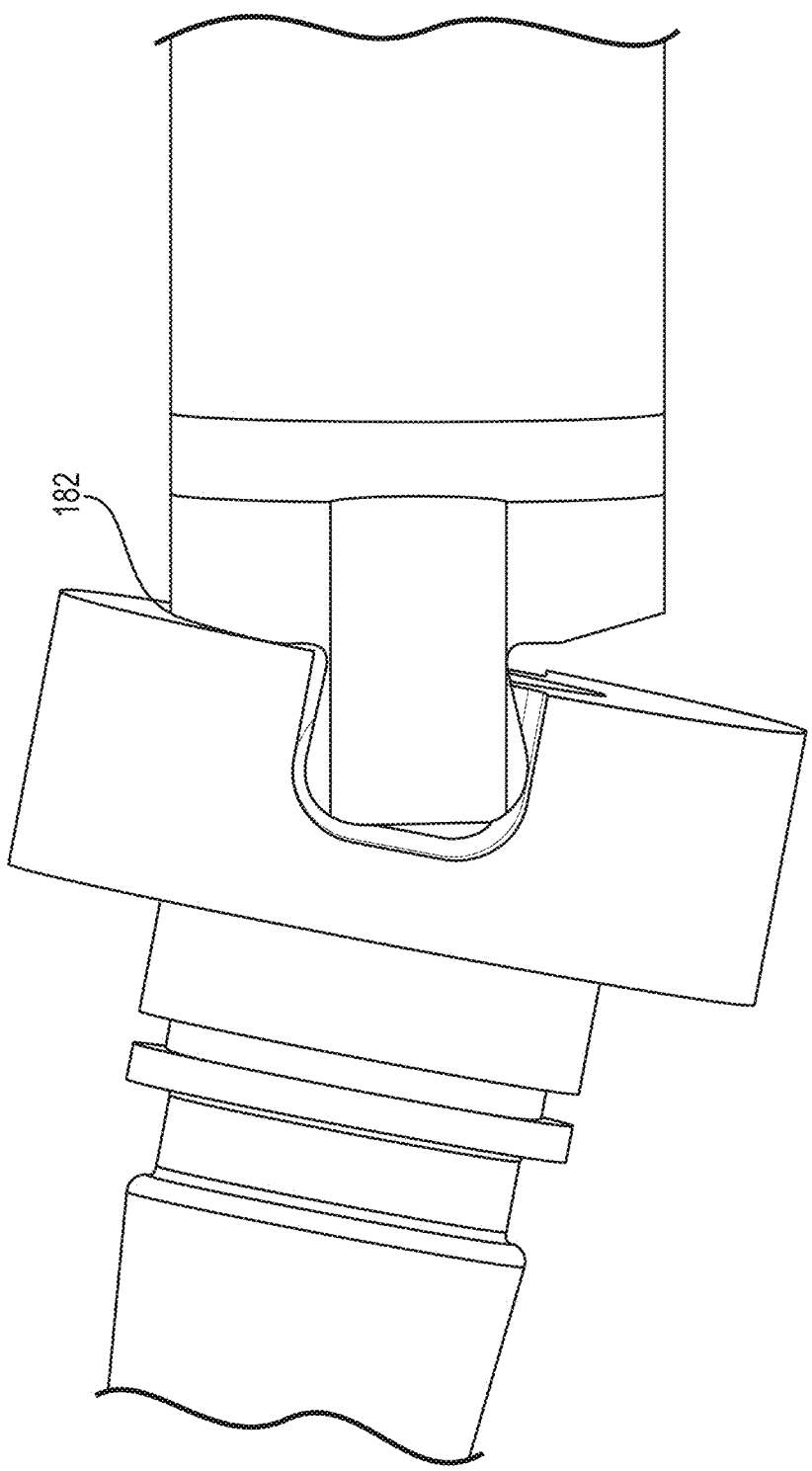
FIG. 19 depicts a perspective view of an embodiment of the present invention.

In an alternate embodiment of hybrid device 17, depicted in FIGS. 18 and 19, the device may include an angulation feature 182 that provides for angulation between first spacer body 170 and second spacer body 172. Angulation feature 182 allows device 18 to accommodate variations in a patient's anatomy and/or to accommodate the curvature at the L5-S1 junction. Angulation feature 182 may be a mechanical connection such as depicted in FIG. 18 or a flexible material such as nitinol, as depicted in FIG. 19 or any other suitable angulation feature.

Hybrid device 17 may be inserted into an intervertebral space in an unexpanded position and expanded in situ by the insertion of fill material into container 174 and/or by mechanical tools.

The entire disclosure of U.S. patent application Ser. No. 13/557,993, filed Jul. 25, 2012, entitled FAR LATERAL SPACER, is hereby incorporated by reference herein.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A method of placing an implant for intervertebral fusion between adjacent vertebral bodies in a patient, wherein the implant comprises a first intervertebral spacer body, a second intervertebral spacer body spaced apart from the first spacer body and an expandable container disposed between the first intervertebral spacer body and the second intervertebral spacer body, and wherein the first spacer body defines a height dimension perpendicular to respective endplates of the adjacent vertebral bodies, the method comprising:

inserting the implant in a space between the adjacent vertebral bodies so that the implant is oriented such that respective opposing surfaces of the first intervertebral spacer body and the second intervertebral spacer body respectively contacts both of the adjacent vertebral bodies simultaneously, wherein the first intervertebral spacer body has a non-adjustable fixed height; and filling the expandable container with fill material such that the expandable container expands to mutually contact both of the adjacent vertebral bodies.

2. The method of claim 1, wherein the step of filling the expandable container includes filling the expandable container with bone graft material.

3. The method of claim 1, wherein the step of filling the expandable container includes introducing the fill material through a fill port.

4. The method of claim 1, wherein the step of filling the expandable container includes introducing the fill material through a fill port defined through the first intervertebral spacer body.

5. The method of claim 1, wherein the step of filling the expandable container includes:

introducing the fill material through a fill port defined through the first intervertebral spacer body; and passing the fill material through a connecting rod to communicate the fill material into the expandable container, wherein the connecting rod is coupled to the first intervertebral spacer body and extends to the second intervertebral spacer body.

6. The method of claim 1, wherein the step of filling the expandable container with fill material moves the first intervertebral spacer body and the second spacer body apart from one another in a direction parallel to respective endplates of the adjacent vertebral bodies.

7. The method of claim 1, wherein the expandable container comprises a mesh material.

8. The method of claim 1, wherein the expandable container is porous.

9. The method of claim 1, wherein the step of inserting the implant in a space between the adjacent vertebral bodies is performed via minimally invasive surgical (MIS) techniques.

10. The method of claim 1, further comprising engaging at least one of the adjacent vertebral bodies with an outward projection defined on at least one of the first intervertebral spacer body and the second intervertebral spacer body.

11. The method of claim 1, wherein the implant is inserted between the adjacent vertebral bodies in a direction parallel to respective opposing end plates of the adjacent vertebral bodies.

12. The method of claim 1, further comprising defining a fill opening into the expandable implant through at least one of the first intervertebral spacer body and the second intervertebral spacer body.

13. The method of claim 1, further comprising connecting the first intervertebral spacer body to the second intervertebral spacer body via a connecting rod spanning therebetween, wherein the connecting rod passes through the expandable container.

14. The method of claim 13, wherein the connecting rod includes at least one fill opening in communication with an interior of the container.

15. The method of claim 1, further comprising angling the first spacer body with respect to the second spacer body in a plane defined parallel to opposing end plates of the respective adjacent vertebral bodies.

16. The method of claim 1, wherein the expandable container comprises of a conformable material.

17. The method of claim 1, further comprising engaging at least one of the adjacent vertebral bodies with a textured surface defined on side of at least one of the first intervertebral spacer body and second intervertebral spacer body that faces the adjacent vertebral body being engaged.

18. The method of claim 1, wherein the expandable container portion is filled with fill material sufficiently to distract the adjacent vertebral bodies.

19. The method of claim 1, wherein the step of filling the expandable container portion with fill material moves the first intervertebral spacer body and the second spacer body apart from one another.

20. The method of claim 1, further comprising engaging at least one of adjacent vertebral bodies with a projection extending outward from at least one of the respective opposing surfaces of the first intervertebral spacer body and the second intervertebral spacer body.

* * * * *